United States Patent [19]
Boebel et al.

[11] Patent Number: 5,385,568
[45] Date of Patent: Jan. 31, 1995

[54] SURGICAL INSTRUMENT FOR MANIPULATING A THREAD

[75] Inventors: Manfred Boebel, Oethisheim; Hossein Messroghli, Gross Gerau, both of Germany

[73] Assignee: Richard Wolf GmbH, Knittlingen, Germany

[21] Appl. No.: 165,011

[22] Filed: Dec. 10, 1993

Related U.S. Application Data

[63] Continuation of Ser. No. 961,172, Oct. 14, 1992, abandoned.

[30] Foreign Application Priority Data

Oct. 14, 1991 [DE] Germany ............................ 4133966

[51] Int. Cl.$^6$ .............................................. A61B 17/00
[52] U.S. Cl. ...................................... 606/144; 606/228
[58] Field of Search ............... 606/106, 107, 113, 138, 606/144, 148, 160, 228, 232

[56] References Cited

U.S. PATENT DOCUMENTS

| | | | |
|---|---|---|---|
| 601,123 | 3/1898 | Chaoe | 223/104 |
| 4,008,913 | 3/1977 | Cole | 289/17 |
| 4,102,478 | 7/1978 | Samoilov . | |
| 4,602,635 | 7/1986 | Mulhollan et al. . | |
| 4,606,335 | 8/1986 | Wedeen . | |
| 4,641,652 | 3/1987 | Hutterer et al. | 606/148 |

FOREIGN PATENT DOCUMENTS 1527083 4/1967 France .

*Primary Examiner*—John D. Yasko
*Attorney, Agent, or Firm*—Cohen, Pontani, Lieberman, Pavane

[57] ABSTRACT

A surgical instrument is provided for manipulating a thread situated within a body, in particular a body cavity. It has a shaft with a handle on the proximal end of the shaft and two thread receivers on the distal end of the shaft. Each thread receiver is formed by an open guide at least partly surrounding the thread and which may consist of wire. The openings of the two thread receivers are arranged facing in opposite directions, so that the thread may be pulled as well as pushed using the instrument.

8 Claims, 1 Drawing Sheet

SURGICAL INSTRUMENT FOR MANIPULATING A THREAD

This is a continuation of U.S. application Ser. No. 07/961,172, filed Oct. 14, 1992 now abandoned.

FIELD OF THE INVENTION

The invention relates to a surgical instrument for manipulating a thread situated within a body, in particular a body cavity, having a shaft with a handle at the proximal end of the shaft and with a thread receiver at the distal end of the shaft.

BACKGROUND OF THE INVENTION

Surgical instruments of this type are used, for example when ligating a blood vessel, organ or the like. In the case of such surgical—usually endoscopic—operations, a thread or a loop is initially introduced into the body or into the body cavity via a first puncture channel. This thread is then placed at the required point within the body cavity by means of a surgical instrument or thread manipulator of the afore-mentioned type. The thread manipulator is usually introduced into the body cavity via a further puncture channel, for example via the instrument channel of an endoscope or another insertion sleeve.

In accordance with the state of the art, gripping forceps are usually used as a thread manipulator. They have two handles at the proximal end which are connected to the mouth part arranged at the distal end by means of a shaft with an actuation device arranged therein. The handling of a thread or a loop within the body cavity using gripping forceps of this type is problematic in certain circumstances. Since the thread material is inherently relatively stiff per se, it is wet with liquid when it is introduced into the body cavity and then becomes very unstable as a result of absorbing moisture. In addition, it becomes sensitive to plastic deformations and damage, as a result of which the guaranteed strength values of the thread material may be impaired so as to be unusable. Since the mouth force in gripping forceps of this type is not usually limited, in practice damage to the thread may easily occur. Moreover, handling of the gripping forceps requires some skill, since two handles have to be operated. This requires awkward gripping of the handles of the gripping forceps, particularly when turning the thread.

SUMMARY OF THE INVENTION

In the light of this state of the art, an object of the invention is to design a generic surgical instrument for manipulating a thread situated within the body, so that simple and safe handling is ensured without the danger of damaging the thread.

This object is achieved according to the invention in that two thread receivers are provided at the distal shaft end of the instrument, each of which is formed by an open guide at least partly surrounding the thread and the receiver openings of which are arranged to be in opposite directions.

Both shear and tensile forces may be exerted on the thread by the opposed receiving openings. Simple and at the same time safe manipulation of the thread is possible in conjunction with the guide partly surrounding the thread, preferably by at least 180°. The thread manipulator of the invention need only be operated using one handle. Its operation is particularly simple since the whole of the instrument may be rotated about its longitudinal axis and/or displaced in axial direction using this handle. Damage to the thread to be manipulated by the instrument is virtually impossible using an appropriate design, since the thread is only guided within the receivers, but no lateral compressive forces are exerted on the thread, as is the case, for example using forceps. There are also considerable savings in production costs compared to instruments according to the state of the art as a result of the simple design of the instrument of the invention. The receiver of the invention may be made in its simplest form from an appropriately Shaped wire extending in the distal direction with respect to the shaft.

Advantageously, the thread receivers may be formed as hook-shaped structures, since on the one hand this facilitates secure guiding due to adequate wrap-around of the thread, and on the other hand problem-free release of the thread.

When forming the thread receivers from wire, the shaft may merge continuously into the wire cross-section, so that a thread running along the shaft is guided virtually automatically into one of the receivers during axial displacement of the shaft.

The receiver openings are preferably arranged parallel to the shaft axis, so that a thread lying in front of the instrument or on the instrument is guided into the receiver when moving the shaft in the axial direction.

A preferred embodiment of the instrument consists in the arrangement of an S-shaped wire on the end of the shaft. Depending on the application, other embodiments may also be advantageous, for example an approximately C-shaped bent wire on the end of the shaft. It is advisable to design the receivers as a type of eye, so that the thread situated therein is completely surrounded on the peripheral side by both receivers, in particular for those applications in which the thread has to be placed within the body cavity with several changes of direction. The instrument is then rotated slightly and displaced axially to admit or remove the thread in order for the thread to be guided through the opening situated in a further plane. The wire forming the receivers thus has an approximately helical course at the distal end of the shaft.

It is advantageous in all embodiments to arrange the receivers so that they lie within the outer contour of the shaft seen in the axial direction thereof. This ensures problem-free introduction of the receivers through an insertion instrument. There is no danger of damage to the receivers during insertion, since the receivers are, as far as possible, not stressed even after a short insertion path if the shaft comes to rest against the insertion sleeve.

DETAILED DESCRIPTION OF THE INVENTION

Figure 1:
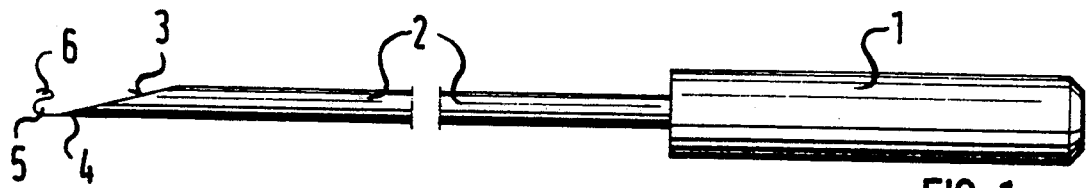
FIG. 1 shows a side view of a thread manipulator according to one embodiment of the invention.

The thread manipulator shown in FIG. 1 has an elongated, substantially cylindrical handle 1 which forms the proximal end of a shaft 2 and is rigidly connected to the shaft.

The shaft 2 is designed to taper continuously towards its distal end 4 in its distal end region 3. It is tapered such that the distal end 4 of the shaft lies eccentrically within the outer contour of the rest of the shaft.

Figure 2:
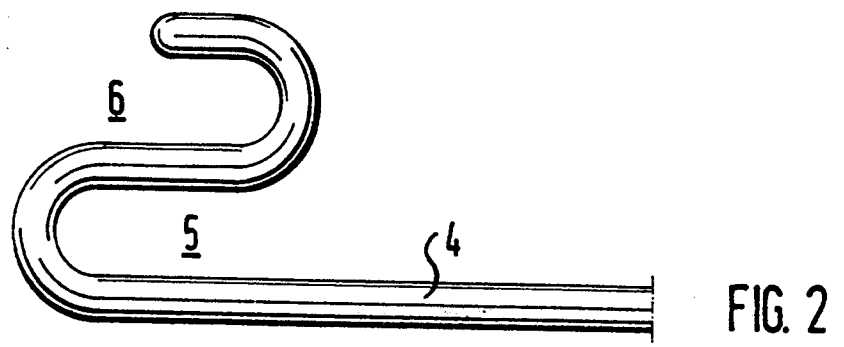
FIG. 2 shows the distal end of the thread manipulator shown in FIG. 1 on an enlarged scale.

Two thread receivers 5 and 6, which are formed by an S-shaped piece of wire shaped onto the end 4 of the shaft, are arranged at this distal end 4 of the shaft. The receivers 5, 6 each comprise a guide in the form of a structure arranged to partly surround the thread. They have opposed openings and are arranged next to one another as shown in FIG. 2. Hence, the receiver 5 is designed to be open in the direction of the proximal end of the shaft and the receiver 6 is designed to be open in the opposite direction. A thread situated therein may be drawn in the direction towards the proximal end of the instrument, for example using the receiver 5 shown in FIG. 2, and pushed in the opposite direction using the receiver 6. Since the angle of wrap-around of the receivers is approximately 180° and the lateral ends of the receivers lying parallel to the shaft 2 are designed to be extended, there is also secure lateral guiding of the thread without there being problems when releasing the thread from the manipulator.

Figure 3:
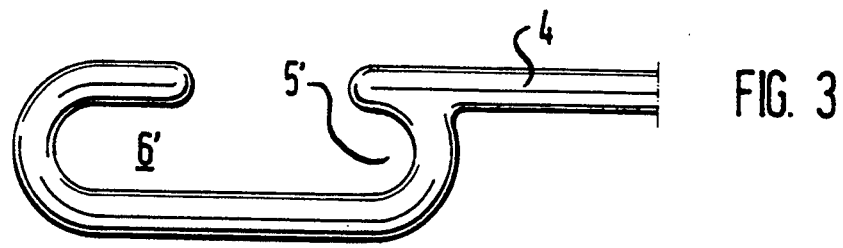
FIG. 3 shows the distal end of another embodiment of a thread manipulator represented according to FIG. 2.

FIG. 3 shows another embodiment in which the receivers 5' and 6' are not arranged next to one another as in the previous example, but are arranged to be opposite each other. The piece of wire arranged on the distal end 4 of the shaft is designed in this embodiment to be substantially C-shaped, so that a thread may be removed laterally after passing from the particular receiver opening of the receivers 5' and 6'.

Figure 4:
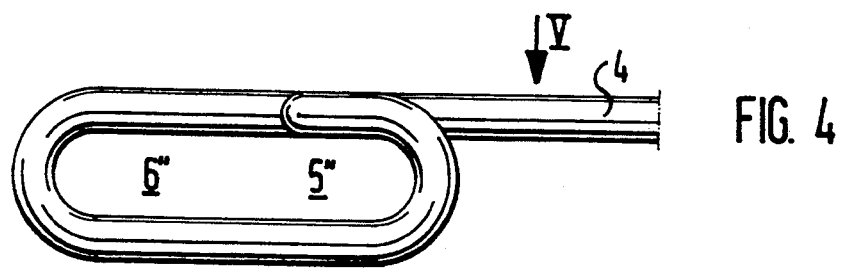
FIG. 4 shows the distal end of yet another embodiment of a thread manipulator represented according to FIG. 2.
Figure 5:
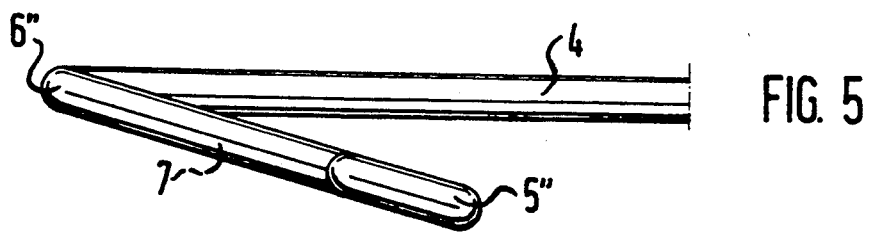
FIG. 5 shows a view in the direction of the arrow V in FIG. 4.

A third embodiment is shown in FIGS. 4 and 5. The receivers 5" and 6" shown in this arrangement are designed to be opposing with openings pointing towards one another as in the embodiment according to FIG. 3. However, the particular openings of the receivers 5", 6" emerge directly in the opening of the opposing recess 6" or 5", so that the thread does not pass out of the instrument when changing direction, but passes into the other receiver. An inlet and outlet opening 7 is formed, in that the wire forming the receivers 5" and 6" is arranged to be substantially helical, so that an opening 7 is produced between the planes set by the wire.

All embodiments of the invention described hereinabove are designed in the region of their receivers such that they lie within the outer contour of the shaft 2 (seen in the axial direction of the shaft 2). This ensures problem-free passage through an insertion instrument, for example an endoscope.

In the embodiments described, the receivers are made from wire. However, it is obvious that they may also be formed from sheet metal or in any other suitable manner, for example by casting.

What is claimed is:

1. A surgical instrument for manipulating a thread situated within a body, in particular a body cavity, comprising a shaft having a proximal end and a distal end, a handle located at said proximal end of the shaft, and two thread receivers located at said distal end of the shaft, each of said thread receivers being formed by a hook-shaped structure having an opening and being arranged to at least partly surround the thread, said openings being arranged to face in opposite directions and said hook-shaped structures being arranged to lie directly adjacent one another in a single, common plane.

2. A surgical instrument as claimed in claim 1, wherein said thread receivers are formed from wire.

3. A surgical instrument as claimed in claim 1, wherein said thread receivers comprise an S-shaped structure, one end of which continuously merges into the distal end of said shaft.

4. A surgical instrument for manipulating a thread situated within a body, said instrument comprising a shaft having a proximal end and a distal end, a handle located at said proximal end and two thread receivers located at said distal end, each of said thread receivers being formed by an open guide arranged to at least partly surround the thread, one of said guides being open in the direction of said proximal end and the other of said guides being open in the direction of said distal end, said guides being arranged so as to be accessible from a common side of the shaft.

5. A surgical instrument for manipulating a thread situated within a body, in particular a body cavity, comprising a shaft having a proximal end and a distal end, a handle located at said proximal end of the shaft, and two thread receivers located at said distal end of the shaft, each of said thread receivers being formed by a hook-shaped structure so as to form an opening and being arranged to at least partly surround the thread, said openings being arranged to face in opposite directions and to lie in a direction parallel to the axis, and said hook-shaped structures being arranged to lie directly adjacent one another in a single, common plane.

6. A surgical instrument for manipulating a thread situated within a body, in particular a body cavity, comprising a shaft having a proximal end and a distal end, a handle located at said proximal end of the shaft, and two thread receivers located at said distal end of the shaft, each of said thread receivers being formed by a hook-shaped structure having an opening and being arranged to at least partly surround the thread, said openings being arranged to face in opposite directions and said hook-shaped structures being arranged to lie directly adjacent one another in a single, common plane, said thread receivers being arranged to lie within an outer contour of said shaft as seen in the axial direction thereof.

7. A surgical instrument for manipulating a thread situated within a body, in particular a body cavity, comprising a shaft having a proximal end and a distal end, a handle located at said proximal end of the shaft, and two thread receivers located at said distal end of the shaft, each of said thread receivers being formed by a hook-shaped structure having an opening and being arranged to at least partly surround the thread, said openings being arranged to face in opposite directions and so as to face one another, and said hook-shaped structures being arranged to lie directly adjacent one another in a single, common plane.

8. A surgical instrument for manipulating a thread situated within a body, in particular a body cavity, comprising a shaft having a proximal end and a distal end, a handle located at said proximal end of the shaft, and two thread receivers located at said distal end of the shaft, each of said thread receivers being formed by a hook-shaped structure having an inlet opening and an outlet opening for the thread and being shaped so as to completely surround the thread and form guides for the inlet and outlet opening that extend over several planes transverse to the thread axis, said openings being arranged to face in opposite directions.

* * * * *